United States Patent
Ludwig et al.

(10) Patent No.: US 6,225,094 B1
(45) Date of Patent: May 1, 2001

(54) METHOD FOR THE GENUS-SPECIFIC OR/ AND SPECIES-SPECIFIC DETECTION OF BACTERIA IN A SAMPLE LIQUID

(75) Inventors: Wolfgang Ludwig, Sachsenkam; Karl-Heinz Schleifer, Unterschleissheim; Christoph Kessler, Dorfen; Ruediger Rueger, Seeshaupt; Anne Stern, Penzberg, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/073,985

(22) Filed: Jun. 8, 1993

Related U.S. Application Data

(63) Continuation of application No. 07/772,026, filed on Oct. 8, 1991, now abandoned.

(30) Foreign Application Priority Data

Oct. 9, 1990 (DE) .................................. 40 32 024
Dec. 5, 1990 (DE) .................................. 40 38 804

(51) Int. Cl.$^7$ .............................. C12P 19/34; C12Q 1/68
(52) U.S. Cl. ................... 435/91.51; 435/91.2; 435/91.1; 435/6
(58) Field of Search ............... 536/24.3, 24.33; 735/78; 935/76–78

(56) References Cited

U.S. PATENT DOCUMENTS 4,683,195 * 7/1987 Mullis et al. ........................ 435/6

FOREIGN PATENT DOCUMENTS

| 0 307 270 | 3/1989 | (EP) . |
| 0 332 435 | 9/1989 | (EP) . |
| 0 333 465 | 9/1989 | (EP) . |
| 0 420 260 | 4/1991 | (EP) . |
| 2 202 328 | 9/1988 | (GB) . |
| 8803957 * | 2/1988 | (WO) . |
| WO 90/11374 | 10/1990 | (WO) . |

OTHER PUBLICATIONS

Wu et al. Proc. Natl. Acad. Sci. USA vol. 86, p. 2757–2760 (1989).
Gibbs et al. Nucl. Acids. + Res. vol. 17, p. 2437–3448 (1989).
Frohman et al, Proc. Natl. Acad.Sci., USA, vol. 85, (Dec., 1988) pp. 8998–9002.*

* cited by examiner

*Primary Examiner*—Bradley L. Sisson
(74) *Attorney, Agent, or Firm*—Arent Fox Kintner Plotkin & Kahn, PLLC

(57) ABSTRACT

For the genus-specific or/and species-specific detection of bacteria in a sample liquid, bacterial RNA is hybridized with a primer which is complementary to a genus-specific or species-specific region of the RNA of particular bacteria or to a highly conserved region of the RNA of bacteria in general, but which is not complementary at its 3' end to the RNA of bacteria of another genus or species, the primer is elongated in the presence of a suitable polymerase and the four deoxyribonucleotides, if desired, with a concurrent or subsequent labelling of the elongation product and an elongation product formed is hybridized with a genus-specific or species-specific oligonucleotide after denaturation and the hybridization is detected by means of the oligonucleotide label.

22 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:1:

CGGTTAAGAA CGCTCTCCTA CCATTT      26

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:2:

AGAACGCTCC CCTACC      16

(2) INFORMATION FOR SEQ ID NO:3:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:3:

TGCGTAATAG CTCACT      16

(2) INFORMATION FOR SEQ ID NO:4:

```
        (i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:4:

TTCGCTCGCC GCTACTT                                                    17

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:5:

CTAGCAGTTA TTCATGAGTG                                                 20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:6:

CTCACTTCTT AACGCTCCAG                                                 20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:7:

AGCGTTGGAT TCAATTTAAT                                                 20
```

METHOD FOR THE GENUS-SPECIFIC OR/ AND SPECIES-SPECIFIC DETECTION OF BACTERIA IN A SAMPLE LIQUID

This application is a continuation of application Ser. No. 07/772,026 filed Oct. 8. 1991 now abandoned.

The invention concerns a method for the genus-specific or/and species-specific detection of bacteria in a sample liquid.

After the development of hybridization techniques many methods were developed for the detection of certain nucleic acids which could be used to detect the presence or absence of particular nucleic acid segments. These methods also encompass the diagnosis of human hereditary diseases as well as of other defects at the genome level which do not necessarily lead to an actual effective disease. However, the nucleic acid tests based on the initially developed methods did not have a very high specificity and there were difficulties with respect to the accuracy of the detection in particular when testing for mutations on nucleic acids which only affected a few bases. In particular the known hybridization methods were too unspecific for the differentiation of nucleic acid variants which merely differed in one or two bases. The reason for this was firstly that very stringent conditions could not be used for the hybridization because of the use of relatively short oligonucleotides which is why the absence of hybridization of one base (a so-called "mismatch") could usually not be detected. Another reason was the availability of often only relatively small amounts of purified nucleic acid or nucleic acids to be differentiated.

The PCR reaction was developed among others as part of the further development of the nucleic acid detection methods and can be used to amplify a nucleic acid to be detected. However, by-products are often formed in the PCR reaction which interfere with the subsequent detection by hybridization. Therefore a method was already suggested in EP 0 332 435 in which, in order to differentiate between nucleic acids which differ by at least one nucleotide, a diagnostic primer is used which is elongated with the aid of a polymerase and the nucleoside triphosphates, whereby, however, an elongation only takes place when the 3' terminal nucleotide of the primer is complementary to the corresponding nucleotide of the nucleic acid to be detected. The presence of a possible point mutation variant is determined in this method via the presence or absence of an elongation product. This is shown in this application using particular hereditary diseases in humans as an example.

However, there are also difficulties in this technique in that some polymerases have a so-called "proof reading activity" which corrects the mismatch during the primer elongation and thus make a specific detection impossible. It was therefore still necessary to develop a method with which differences of only one base on nucleic acids can be detected reliably. In particular there was a need for a highly specific detection method for nucleic acid variants in order to detect the presence or absence of particular bacterial genera and to differentiate between them in a sample liquid. The object of the invention was therefore to provide such a highly specific method.

The invention therefore concerns a method for the genus-specific or/and species-specific detection of bacteria in a sample liquid in which bacterial RNA is hybridized with a primer which is complementary to a genus-specific or species-specific region of RNA of particular bacteria but which is not complementary at its 3' end to the RNA of bacteria of another genus or species, the primer is elongated in the presence of a suitable polymerase and the four deoxyribonucleotides, if desired, with a concurrent or subsequent labelling of the elongation product whereby an elongation product which forms when the primer and template RNA are complementary is additionally hybridized, after denaturation, with a genus-specific or species-specific oligonucleotide and the hybridization is detected by means of the oligonucleotide label.

Within the scope of the invention the primer can also be complementary to a region of the RNA of bacteria which is in general highly conserved provided that a mismatch results at the 3' end of the primer when it is base paired with the RNA of the other genus or species.

Within the scope of the invention the term "bacterial RNA" also includes an amplification product of the RNA which is directly formed by the bacteria. The amplification of the bacterial RNA can be carried out using known methods such as e.g. polymerase chain reaction (U.S. Pat. No. 4,683,195), nucleic acid sequence based amplification (EP-A 0 329 822) or fast enzyme linked intense chain replication effect (German Patent Application P 39 29 030.1).

Since two selection steps are used in the method according to the present invention it is possible to considerably reduce the risk of erroneous results caused by only one differentiating reaction and thus the method provides a highly specific test which can be used to differentiate between bacterial RNAs which only differ in a few bases which in turn allows a statement about the presence of a particular bacterial genus or species. Indeed it is particularly the 16S-rRNA and also the 23S-rRNA of bacterial species which often only differ in a few nucleotides. Such differences are often the only possibility of differentiating between "harmful" and "harmless" bacteria. In principle also a differentiation of individual bacterial families can be carried out according to the present invention.

In a particular preferred embodiment of the invention it is possible to determine the actual species in virtually one step after an examination for the presence of members of a genus of bacteria. A primer is used for this which is complementary to the RNA of a particular genus of bacteria but which differs from the RNA of bacteria of other genera by at least one and preferably two or three bases at its 3' end. If bacteria of the genus being searched for are present in the sample liquid, an elongation product is formed after primer elongation and this elongation product is then hybridized with an oligonucleotide which corresponds to another region of the bacterial RNA whereby in this case the requirements for hybridization are only met for a particular species of this bacterial genus.

In the method according to the present invention it is possible to use very long primers for the hybridization of the RNA with the primer which in turn allows the use of very stringent conditions in this hybridization. As a result the primer elongation step already yields a very specific result which is substantially increased by the additional hybridization step. According to the present invention it is also possible to run additional control experiments in which primers or oligonucleotides are used which are complementary or identical to regions on the RNA which are the same for many bacterial genera and species. For control experiments there are even primers or oligonucleotides which are specific for all eubacteria. The presence and accessibility of the target RNA can be demonstrated by such control experiments and thus prevents "false negative" results. In addition blind experiments without target RNA can be carried out. By this means it is possible to avoid mistaking artefacts in the primer elongation as well as in the hybridization for the actual specific reaction. At the same time the amounts of bacteria of a particular genus or species can be estimated in-relation to the total amount of bacteria.

According to the present invention any RNA which can be shown to be different in different genera or species can be used as the RNA of bacterial origin.rRNA, mRNA or t-RNA is preferably used by selecting primers and oligonucleotides for the method according to the present invention which are complementary to them. Bacterial RNA is prepared for the method according to the present invention according to known methods.

The actual detection of the hybridization of the elongation product formed is carried out via the oligonucleotide label whereby any type of label for nucleic acids can be used in this case. According to the present invention the elongation product can in addition be labelled in order to also observe this reaction; the labelling can either be carried out during its formation or subsequently or it can be labelled via the primer. The labelling of the elongation product is preferably carried out by using a primer which is already labelled.

It is particularly preferred according to the present invention that the labelling of the primer and of the oligonucleotide is different and that thus both steps in the procedure can be controlled and monitored separately.

The elongation products are prepared for the hybridization in a well-known manner, preferably by separating non-elongated primers and non-reacted nucleic acid components. All methods are suitable for this which lead to a separation of the nucleic acid fragments by size. This is preferably carried out using gel electrophoresis or ascending thin layer chromatography. Separation by HPLC also appears suitable.

The hybridization with the oligonucleotide is then also carried out in a well-known manner such as e.g. by Southern transfer of the DNA onto a nitrocellulose paper or by other known methods. The necessary conclusions can then be drawn from the location of the signal after hybridization with the oligonucleotide as well as from the signal strength.

Within the scope of the invention it is, however, also possible and also preferred to carry out a double labelling of elongation product and oligonucleotide in such a way that an elongation product formed is bound via its label to a solid phase and the detection is then carried out by means of an oligonucleotide in labelled form which is not complementary to the non-elongated primer and thus cannot result in a erroneous signal. For such labels binding pairs are for example suitable such as biotin/streptavidin or hapten/anti-hapten antibody, such as digoxigenin/anti-digoxigenin antibody in which a binding partner is coupled to the solid phase (e.g. streptavidin) and the second partner is bound to the primer or to one of the nucleic acid building blocks.

In order to increase the specificity of the method according to the present invention, the hybridization with the oligonucleotide takes place on a sequence which is different from the primer sequence. This sequence can be at a distance from the primer sequence such as the corresponding nucleic acid chain lengths which are usually produced by primer elongation methods. The hybridization is preferably carried out with a sequence which is near to the sequence on the RNA complementary to the primer and is at a distance to it of 20 to 400 bases in the 5' direction.

Within the scope of the method according to the present invention a primer is preferably used which is 15 to 50 nucleotides long whereby the length of the primer is, however, primarily dependent on the hybridization conditions and thus on the stringency of the process which is in turn dependent on the temperature sensitivity of the polymerase used which is preferably AMV or MMuLV (Avian Myeloblastosis Virus and Moloney Murine Leukemia Virus, respectively) reverse transcriptase. The hybridization temperature may not be higher than the temperature tolerated by the polymerase but should, however, be high enough to enable a high stringency. The longer the primer is, the higher is the melting temperature of the hybrid product of primer and RNA sequence to be detected.

The oligonucleotide used for the hybridization with the elongation product is preferably 12 to 20 nucleotides long within the scope of the invention which on the one hand achieves a high specificity and on the other hand nevertheless keeps the demands on the oligonucleotide synthesis relatively low.

The method according to the present invention allows the presence of particular bacteria to be detected in a highly specific manner in a sample liquid. In particular it is possible in this process to also determine the actual subspecies at the same time when a particular bacterial genus is present. The high specificity requirements for clinical diagnosis are also fulfilled.

The following examples are intended to further elucidate the invention.

EXAMPLE 1

Differentiation of *Lactococcus lactis* subspecies *lactis* and *L. lactis* subspec. *cremoris*

Cells of the respective bacterial subspecies (1 to 3 g) were suspended in 3 ml 1×SSC (150 mmol/l NaCl, 15 mmol/l trisodium citrate, pH 7.0 at 0° C.). After lysing the cells with glass beads (50 g; φ 0.17 mm) in a cell homogeniser for 4×30 seconds, a phenol extraction was carried out in which it was shaken out 3× with 3 ml 1×SSC and 6 ml phenol (1×SSC saturated) in each case. This was followed by a four-fold extraction with twice the volume of diethyl ether. Finally the nucleic acids were precipitated by addition of 0.1 volume of 5 mol/l potassium acetate, 2.5 volume absolute ethanol at −20° C. and after centrifugation (20 minutes, 10000 g) the precipitate was dried under vacuum. Remaining DNA was resuspended by suspension in 10 ml 3 mol/l sodium acetate, pH 6.0 at 0° C. in an Ultra Turrax (10 seconds) and after centrifugation and repeating this procedure 3 to 4 times mainly rRNA was obtained as a pellet.

2 μg of the rRNA prepared in this way and 10 pmol primer having the following sequence (SEQ ID NO 1)

5' CGGTTAAGAACGCTCTCCTACCATTT 3' were denatured in 5 ml buffer (0.1 mol/l KCl; 0.05 mol/l Tris-HCl, pH 8.3) for 4 minutes at 90° C. and the mixture was subsequently incubated for 10 minutes at 70° C. 1 μl of this mixture was incubated with 4 μl buffer (0.05 mol/l Tris/HCl, pH 8.3; 0.12 mol/l NaCl, 0.07 mol/l MgCl$_2$; 0.06 mmol/l dGTP, dCTP, dTTP in each case; 0.06 mmol/l [$^{32}$p] α-dATP (about 1 μCi; 5 units AMV or MMuLV reverse transcriptase (Boehringer Mannheim)) for 20 minutes at 45° C. The reaction products (2 μl) were separated by means of ascending thin layer chromatography (DEAE cellulose, Polygram cell 300, Schleicher and Schüll) for 45 minutes at 80° C. using 0.4 mol/l ammonium formate in 9 mol/l urea as the mobile solvent. The elongation products formed could be detected after autoradiography.

As a control of the detection system, a control reaction was carried out as a positive standard using a synthetic oligonucleotide which is complementary to rRNA molecules of almost all bacteria having the sequence (SEQ ID NO 2)

5' AGAACGCTCCCCTACC 3'.

The conditions were the same as those already described for the specific primer.

A sample of the elongation products which were obtained using the specific primer was denatured in 200 μl 0.4 N NaOH (20 minutes, 25° C.) and then bound to a membrane (Zetaprobe, Biorad; dot blot, Minifold, Schleicher and Schüll). The detection probe having the sequence (SEQ ID NO 3)

5' TGCGTAATAGCTCACT 3', whose complementary sequence on the RNA is ca. 65 bases from the complementary sequence to the specific primer on the 5' side (5 pmol) was labelled in 20 μl buffer (0.027 mol/l Tris/HCl, pH 8; 0.011 mol/l DTT; 0.9 mmol/l spermine; 0.011 mol/l MgCl$_2$; 0.25 mmol/l [γ-$^{32}$P] ATP, ca. 30 μCi) by a 30 minute incubation at 37° C. Non-reacted nucleotides were removed and the labelled detection probe purified by use of the system Gene Clean™ or Mer Maid (Bio 101 Inc., La Jolla, USA). The membrane prepared as described above to which the elongation product is bound, was washed in 0.5×SSC, 0.5% SDS for one hour at 50° C. and then pre-incubated in 6×SSC, 5×Denhardt, 0.5% sarcosyl, 0.1% SDS for 2 hours, also at 50° C. The hybridization was carried out with 3 pmol of the detection probe in 6×SSC, 5×Denhardt, 0.5% sarcosyl, 0.1% SDS for 4 hours at 38° C., followed by a wash with 2×SSC, 0.1% SDS (2×5 minutes at 25° C., 1×5 minutes at 37° C.). After autoradiography, a densitometric analysis of the autoradiogram was carried out the result of which showed that after applying the elongation product in the dot blot comparable signals were obtained for the elongation products formed and the control reaction; however, when the detection probe is used this is only the case when *L. lactis* subspec. *lactis* is present.

EXAMPLE 2

Differentiation of *Lactococcus lactis* and *Streptococcus oralis*, test for cDNA with a *L. lactis*-specific detection probe.

The oligonucleotide of 17 bases in length having the sequence (SEQ ID NO 4)

5' TTCGCTCGCCGCTACTT 3' was used as primer which is complementary to RNA of *L. lactis* but which, however, differs from *Steptococcus oralis* RNA in the last base at its 3' end. The RNA preparation as well as the hybridization and primer elongation was carried out as in Example 1. The sequence (SEQ ID NO 5)

5' CTAGCAGTTATTCATGAGTG 3' was used as the specific oligonucleotide which only hybridizes to *L. lactis* RNA which is substantially different from the RNA sequence of *S. oralis*. The hybridization of the elongation product transferred onto a membrane was also carried out as described in Example 1 but at a temperature of 48° C. The detection was carried out as in Example 1 by autoradiography and densitometric analysis.

EXAMPLE 3

Differentiation of *Lactococcus genera* from other enterococci or gram-positive bacteria and the subspecies-specific differentiation of *Lactococcus lactis* subspecies *lactis* and *Lactococcus lactis* subspecies *cremoris*

The sequence (SEQ ID NO 6)

5' CTCACTTCTTAACGCTCCAG 3' was used as primer. This sequence is genus-specific for Lactococci and allows to differentiate this genus from enterococci and other gram-positive bacteria. The RNA preparation as well as the hybridization and primer elongation was carried out as in Example 1. The sequence (SEQ ID NO 7)

5' AGCGTTGGATTCAATTTAAT 3' was used as the specific oligonucleotide for the subspecies *Lactococcus lactis* subspecies *lactis*. The hybridization of the elongation product transferred onto the membrane was again carried out at 38° C. and the subsequent procedure was also as described in Example 1. After autoradiography and densitometric analysis, it was clear in this case that a hybridization only occurred when *Lactococcus lactis* subspecies *lactis* was present and not when the elongation products of *Lactococcus lactis* subspecies *cremoris* were only present.

The documents referred to and described herein are hereby incorporated by reference for the teachings contained therein.

| Sequence protocols | |
|---|---|
| SEQ ID NO 1 | |
| Length of sequence: | 26 bases |
| Type of sequence: | nucleotide sequence (DNA) |
| Type of strand: | single strand |
| Topology: | linear |
| 5' CGGTTAAGAA CGCTCTCCTA CCATTT-3' | |
| SEQ ID NO 2 | |
| Length of sequence: | 16 bases |
| Type of sequence: | nucleotide sequence (DNA) |
| Type of strand: | single strand |
| Topology: | linear |
| 5'-AGAACGCTCC CCTACC-3' | |

-continued

Sequence protocols

SEQ ID NO 3

| Length of sequence: | 16 bases |
| Type of sequence: | nucleotide sequence (DNA) |
| Type of strand: | single strand |
| Topology: | linear |
| 5'-TGCGTAATAG CTCACT-3' | |

SEQ ID NO 4

| Length of sequence: | 17 bases |
| Type of sequence: | nucleotide sequence (DNA) |
| Type of strand: | single strand |
| Topology: | linear |
| 5'-TTCGCTCGCC GCTACTT-3' | |

SEQ ID NO 5

| Length of sequence: | 20 bases |
| Type of sequence: | nucleotide sequence (DNA) |
| Type of strand: | single strand |
| Topology: | linear |
| 5'-CTAGCAGTTA TTCATGAGTG-3' | |

-continued

Sequence protocols

SEQ ID NO 6

| Length of sequence: | 20 bases |
| Type of sequence: | nucleotide sequence (DNA) |
| Type of strand: | single strand |
| Topology: | linear |
| 5'-CTCACTTCTT AACGCTCCAG-3' | |

SEQ ID NO 7

| Length of sequence: | 20 bases |
| Type of sequence: | nucleotide sequence (DNA) |
| Type of strand: | single strand |
| Topology: | linear |
| 5'-AGCGTTGGAT TCAATTTAAT-3' | |

In the claims:

1. A method for genus-specific and/or species-specific detection of bacteria in a sample liquid comprising the steps of:
   a) hybridizing bacterial RNA with a primer which is complementary to a genus-specific region of RNA of a particular bacteria wherein the primer is not complementary at its 3' end to RNA of bacteria from another genus,
   b) elongating said primer in the presence of a suitable polymerase and deoxyribonucleotides to form an elongation product,
   c) hybridizing said elongation product after denaturation with a labeled oligonucleotide which is specific for a particular species within a genus of bacteria, and
   d) detecting any hybridization by means of the labeled oligonucleotide.

2. The method according to claim 1, further comprising the step:
   labeling said elongation products concurrently with the elongation of said elongation products or subsequent to said elongation.

3. The method according to claim 1, wherein said primer is complementary to a genus-specific or species-specific region of rRNA, mRNA or t-RNA.

4. The method according to claim 1, wherein said labeled oligonucleotide is identical to a species-specific region of rRNA, mRNA or t-RNA.

5. The method according to claim 1, wherein said polymerase is AMV-(Avian Myeloblastosis Virus) or MMuLV-(Moloney Murine Leukemia Virus) reverse transcriptase.

6. The method according to claim 1, further comprising the step:
   separating said elongation products according to size using gel electrophoresis or ascending thin layer chromatography before hybridization with the labeled oligonucleotide.

7. The method according to claim 1, wherein hybridization with said labeled oligonucleotide occurs on a sequence which is near to the sequence complementary to the primer and is at a distance from the primer of 20 to 400 bases in the 5' direction.

8. The method according to claim 1, wherein the oligonucleotide is 12 to 20 nucleotides in length.

9. The method according to claim 1, wherein the primer is 15 to 50 nucleotides in length.

10. The method according to claim 2, wherein the label conjugated to said primer and to said oligonucleotide are different.

11. The method according to claim 2, wherein the label of said elongation products is a partner of a specific binding pair and the label of said labeled oligonucleotide is the other partner of said specific binding pair, said other partner is bound to a solid phase and hybridization of said elongation products with said labeled oligonucleotide is carried out on said solid phase.

12. A method for genus-specific and species-specific detection of bacteria in a sample liquid, comprising the steps of:

hybridizing RNA of target bacteria with a primer which is complementary to a genus-specific region of RNA of said target bacteria, wherein the 3' end of said primer is only complementary to the RNA of said target bacteria and not complementary to the RNA of other bacteria in said sample which differ from the genus of said target bacteria;

elongating said primer in the presence of a suitable polymerase and the four deoxyribonucleotides to form an elongation product;

labeling said elongation product concurrently with the elongation of said elongation product or subsequent to said elongation;

hybridizing said elongation product with a species-specific labeled oligonucleotide after denaturation to form a hybridization elongation product; and detecting said hybridization elongation product.

13. The method according to claim 12, wherein said primer is complementary to a genus-specific region of the RNA of said target bacteria and said labeled oligonucleotide is a species-specific oligonucleotide within the genus of said target bacteria.

14. The method according to claim 12, wherein said primer is complementary to a genus-specific or species-specific region of rRNA, mRNA or t-RNA.

15. The method according to claim 12, wherein said labeled oligonucleotide is identical to a species-specific region of rRNA, mRNA or t-RNA.

16. The method according to claim 12, wherein the label conjugated to said primer and to said oligonucleotide are different.

17. The method according to claim 12, wherein said polymerase is AMV-(Avian Myeloblastosis Virus) or MMuLV-(Moloney Murine Leukemia Virus) reverse transcriptase.

18. The method according to claim 12, further comprising the step:

separating said elongation product using gel electrophoresis or ascending thin layer chromatography before hybridization of said labeled oligonucleotide.

19. The method according to claim 12, wherein the label of said elongation product is a partner of a specific binding pair and the label of said labeled oligonucleotide is the other partner of said specific binding pair, said other partner is bound to a solid phase and hybridization of said elongation product with said labeled oligonucleotide is carried out on said solid phase.

20. The method according to claim 12, wherein hybridization with said labeled oligonucleotide is carried out with a sequence which is near to the sequence on the RNA complementary to said primer and is at a distance from said primer of 20 to 400 bases in the 5' direction.

21. The method according to claim 12, wherein 1 to 3 bases at the 3' end of said primer are not complementary to the said RNA of other bacteria in the sample.

22. The method according to claim 19, wherein said specific binding pair is biotin/streptavidin, hapten/anti-hapten antibody or digoxigenin/anti-digoxigenin antibody.

* * * * *